United States Patent [19]

Fly

[11] 4,073,240
[45] Feb. 14, 1978

[54] PORTABLE ANIMAL HOSPITAL TABLE

[76] Inventor: Howard G. Fly, Box 63, Ovando, Mont. 59854

[21] Appl. No.: 737,903

[22] Filed: Nov. 2, 1976

[51] Int. Cl.² .............................................. A47B 9/00
[52] U.S. Cl. ...................................... 108/20; 108/24; 108/145; 108/147; 248/421; 108/31
[58] Field of Search .................. 108/145, 147, 20, 24, 108/29, 28, 31; 248/421

[56] References Cited

U.S. PATENT DOCUMENTS

| | | | |
|---|---|---|---|
| 2,172,941 | 9/1939 | Manning et al. | 108/20 X |
| 2,569,561 | 10/1951 | Friedman | 108/24 X |
| 2,690,366 | 9/1954 | Kimmel | 108/28 X |
| 3,065,344 | 11/1962 | Chervenka | 108/28 X |
| 3,093,836 | 6/1963 | Christensen | 108/24 X |
| 3,203,670 | 8/1965 | Farris | 108/147 X |
| 3,554,598 | 1/1971 | Dunkin | 248/421 X |
| 3,608,462 | 9/1971 | Groshong | 108/147 X |
| 3,820,176 | 6/1974 | Feiertag | 108/147 X |

FOREIGN PATENT DOCUMENTS 630,471  4/1963  Belgium ............................ 248/421

Primary Examiner—Roy D. Frazier
Assistant Examiner—Peter A. Aschenbrenner
Attorney, Agent, or Firm—Arthur L. Urban

[57] ABSTRACT

A portable animal hospital table comprising a plastic bed surface disposed on an upper frame, a radiation shielding layer positioned below said plastic bed surface and carried by said upper frame, a base frame supported on rolling means, pivotally mounted linkage means operatively connecting said upper frame and said base frame, a pressure cylinder and piston mounted on said base frame and pivotally connected to said linkage means, and means for actuating said pressure cylinder and piston.

9 Claims, 6 Drawing Figures

PORTABLE ANIMAL HOSPITAL TABLE

This invention relates to an animal hospital table and more particularly relates to a portable adjustable animal hospital table which permits convenient and accurate positioning of an animal for X-raying, surgery or other treatment.

In the past, for example, it has been customary to X-ray an animal by lifting the animal onto a table which was located adjacent an X-ray machine and after the X-raying was completed the animal had to be removed from the table and placed in a cage. Also, if treatment was required, the animal would have to be carried to an examining or operating table. This great amount of lifting and carrying created problems, particularly in the case of the dead weight of unconscious animals. Pet hospitals are employing more and more women, and many of the women and even some of the men were unable or unwilling to do the required lifting and carrying. This situation often necessitated the employment of extra personnel solely for the task of lifting and carrying of the animals.

The present invention provides a novel portable adjustable animal hospital table which can be conveniently and accurately positioned for X-raying, surgery or other treatment. The table of the invention can be lowered close to the floor so an animal may be assisted onto the table without lifting. The design of the table of the invention permits its use as an operating or examining table and facilitates easy transfer of an animal from the table to a recovery cage. Also, the table design provides convenience and safety during X-raying.

Other advantages and benefits of the invention will be apparent from the following description and the accompanying drawings in which.

Figure 1:
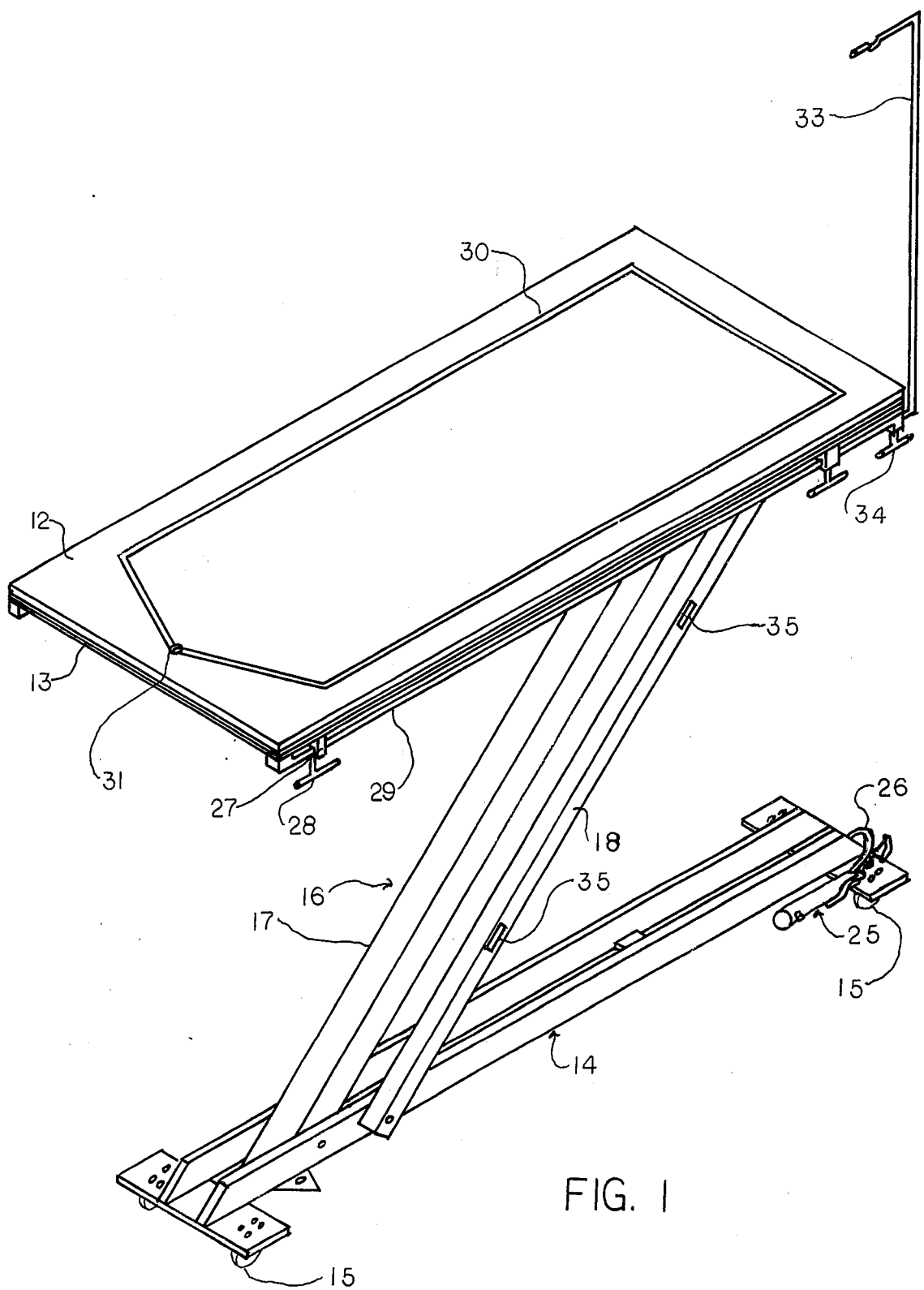
FIG. 1 is a perspective view of one form of the portable adjustable animal hospital table of the present invention.
Figure 2:
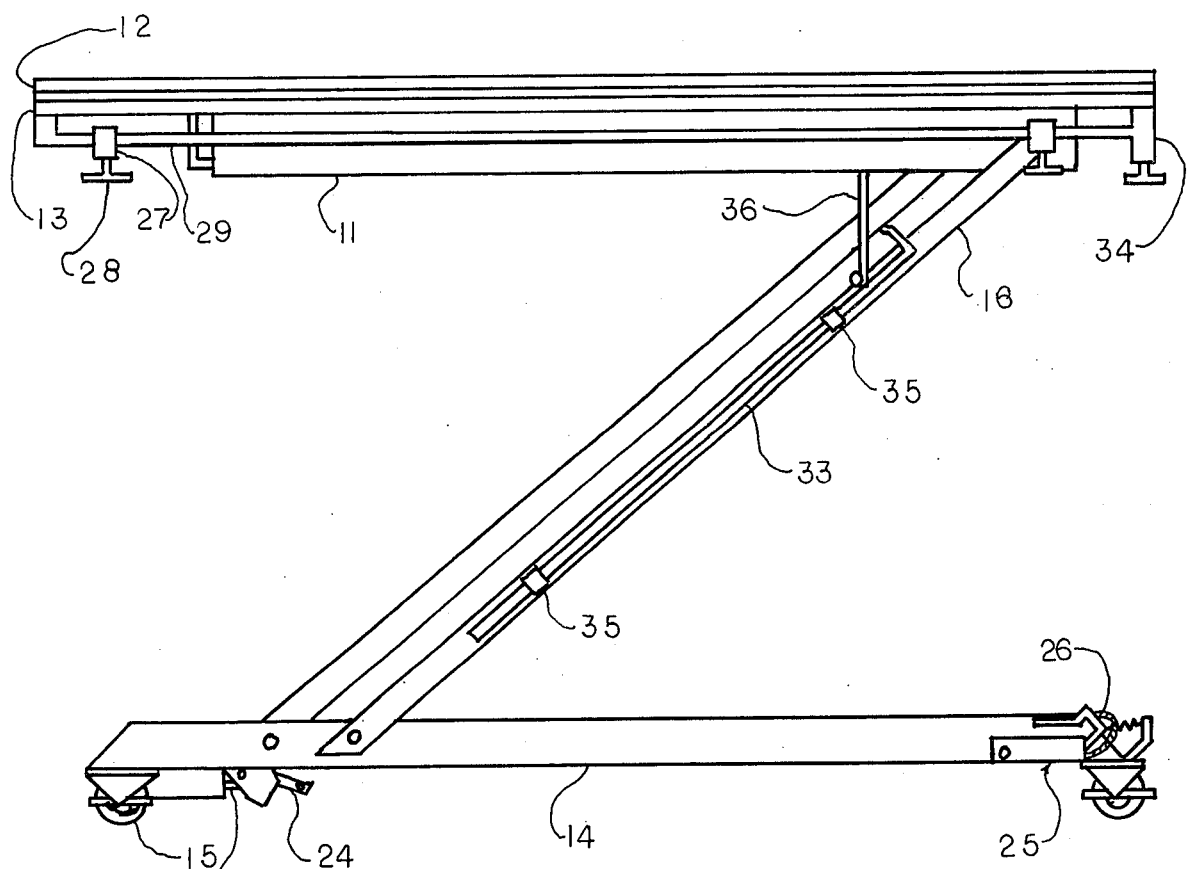
FIG. 2 is a side elevation of the table shown in FIG. 1.
Figure 3:
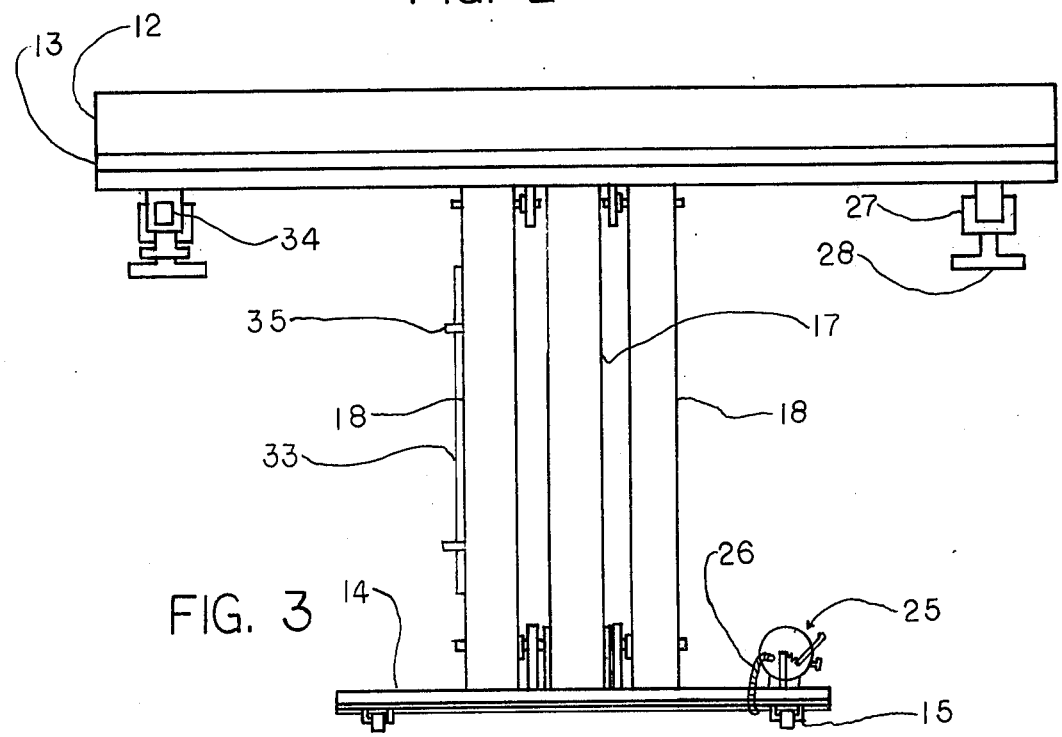
FIG. 3 is a right end view of the table shown in FIG. 2 in a lowered position.
Figure 4:
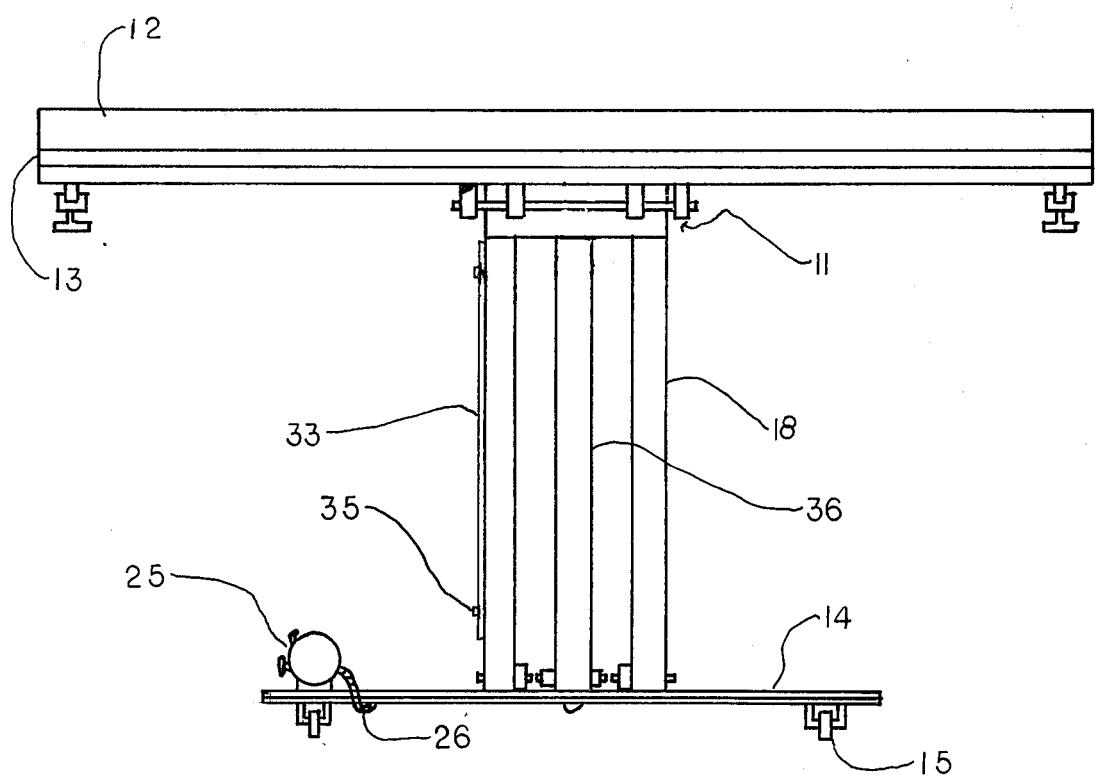
FIG. 4 is a left end view of the table shown in FIG. 2 in a lowered position.
Figure 5:
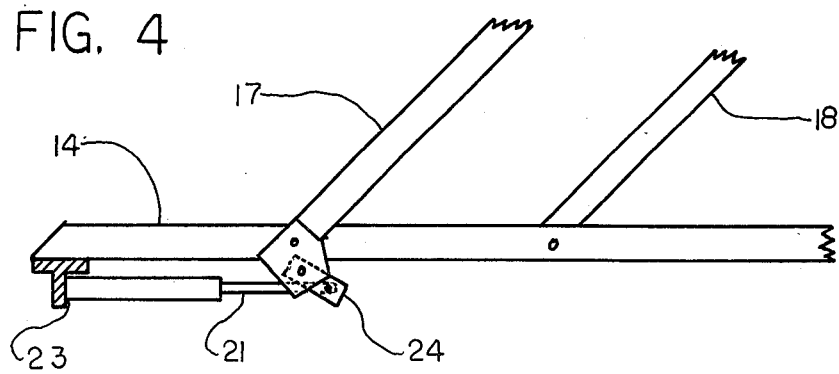
FIG. 5 is an enlarged fragmentary side view of the lower portion of the linkage when the table of FIG. 2 is in a raised position.
Figure 6:
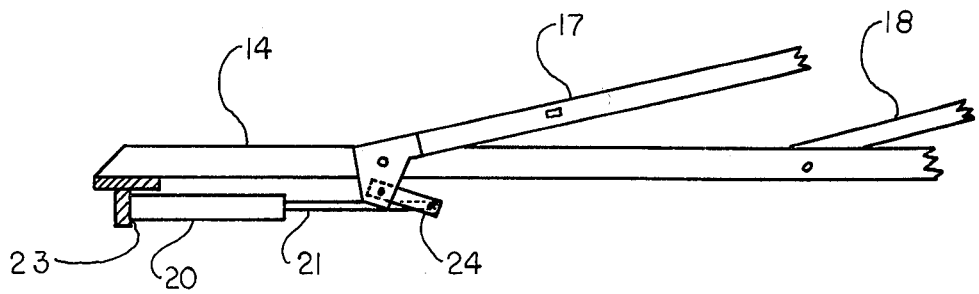
FIG. 6 is an enlarged fragmentary side view of the lower portion of the linkage when the table of FIG. 2 is in a lowered position.

As shown in the drawings, one design of the novel portable adjustable animal hospital table of the invention comprises an upper frame 11 on which is disposed a plastic bed surface 12. A radiation shielding layer 13 is located below the plastic bed surface 12 and carried by the upper frame 11. The table of the invention also includes a base frame 14 which is spaced from the floor by rolling means 15 attached thereto. The rolling means 15 preferably are casters fitted with suitable locks or brakes. The upper frame 11 is adjustably supported above the base frame 14 by linkage means 16 which is pivotally connected both to the upper frame 11 and to the lower base frame 14. The linkage 16 includes a central support member 17 and side stabilizers 18 spaced from the central member toward the longitudinal edges of the upper frame 11 and the base frame 14 and pivotally connected thereto.

The upper frame 11 is raised and lowered with respect to the base frame 14 by pressure cylinder 20 and piston 21. One end of cylinder 20 is attached to base frame 14 and the outer end of piston 21 is pivotally connected to central support member 17 through linkage 24. A pump 25 is operatively connected to cylinder 20 through tubing 26. Advantageously, pump 25 is a foot-operated pump, although other manually or electrically actuated pumps may be employed.

Suitable tie down hardware may be located along the longitudinal edges of upper frame 11. As shown in the drawings, rods 29 are fastened in spaced relationship along the longitudinal edges of the upper frame 11. The rods 29 have slidable bushings 27 with wing bolts 28 threaded therethrough to engage the rod 29 and lock the bushings in the desired position. The wings of bolts 28 provide anchors for fastening tie down straps (not shown).

The plastic bed surface 12 has a groove 30 around the periphery which connects to a drain opening 31. A hanger 33 may be secured to upper frame 11 by clamp 34. An intravenous feeding bottle (not shown) may be hung on the end of hanger 33 so that the animal can be supplied with medication during all of the procedures performed while the animal is on the table. When not needed, the hanger 33 may be detached and stored on stabilizer 18 with clips 35. The table also may include a tilt mechanism 36 to raise one end of the bed surface when required.

In the use of the portable adjustable animal hospital table of the invention as shown in the drawings, upper frame 11 and plastic bed surface 12 attached thereto are lowered close to the floor and an animal is led to the table and pushed onto the bed surface. The animal then is tied to the table with suitable straps (not shown) which are anchored on wing bolts 28 of bushings 27 disposed on rods 29. The bed surface 12 is raised to a desired height by activating pump 25 which actuates cylinder 20 and piston 21. This change in the effective length of piston 21 moves link 24 and forces central support member 17 to pivot with respect to upper frame 11 and base frame 14 to which it is pivotally attached. Since upper frame 11 and base frame 14 are also pivotally connected to the ends of side stabilizers 18, bed surface 12 and upper frame 11 are maintained at the same inclination with respect to the floor during changes in height.

When the desired height is attained, the pump is stopped and the table with the animal secured thereon is moved, for example, to an X-ray machine. At the X-ray machine, the position of the animal with respect to the machine is adjusted by changing the height of the table by activating the pump 25 again. When the correct spacing below the machine is achieved, final alignment of the table is made and the casters 15 locked to prevent accidental movement of the table during X-raying. Since the table has a plastic bed surface 12, preferably formed of a thermoplastic polymer such as a polyalkylene (polyethylene or polypropylene), a polyamide, polyester or polyacrylic polymer or a similar polymer, the bed surface will not show on the X-ray. Also, since the table has a radiation shielding layer 13, the X-ray machine operator will be protected from radiation through the table. After the X-raying is completed, the locks on the casters 15 are released and the table moved away to permit X-raying of a different animal on another table.

If surgery or other treatment is required after the X-rays have been read, the surgery can be performed while the animal is on the same table simply by adjusting the table height to a convenient working level. Blood or body fluids from the animal will flow into groove 30 and through drain opening 31 to a suitable receptacle (not shown). If desired, the bed surface 12 can be tilted by tilt mechanism 36 during surgery. Also, the animal may be given fluids intravenously from a bottle (not shown) hung on hanger 33 supported on clamp 34.

Upon completion of surgery, additional X-rays may be taken while the animal remains on the table and being fed intravenously by moving the table back to the X-ray machine and adjusting the table as described above. When the animal is to be returned to a recovery cage, the table can be moved to the cage and the table height adjusted to a height which will permit the animal to be slid into the cage without lifting.

The above description and the drawings show that the present invention provides a novel portable adjustable animal hospital table with a number of important advantages. The table permits convenient and accurate positioning of an animal for X-raying and/or other treatment including surgery and recovery without necessitating repeated lifting and transfer of the animal from table to table. The animal stays on one table for all treatment when the table of the invention is used. With the table of the invention, the animal can be retained at the same inclination even while the adjustments are being made. Also, since the bed surface of the table is plastic, it does not show on X-rays and in addition minimizes heat loss from the animal body as compared with the stainless steel surfaces employed heretofore. Moreover, the design of the table of the invention improves operator safety due to the radiation shielding layer below the animal supporting bed surface. In addition, the table is simple in design and can be manufactured in quantity relatively inexpensively.

It will be apparent that various modifications may be made in the novel animal hospital table described in detail above and shown in the drawings within the scope of the present invention. For example, the configuration of the plastic bed surface, the linkage means and/or the base frame can be changed for particular requirements. Therefore, the invention is to be limited only by the following claims.

What is claimed is:

1. A portable adjustable animal hospital table comprising a plastic bed surface disposed on an upper frame, a radiation shielding layer positioned below said plastic bed surface and carried by said upper frame, a base frame supported on rolling means, pivotally mounted linkage means operatively connecting said upper frame and said base frame, a pressure cylinder and piston mounted on said base frame and pivotally connected to said linkage means, and means for actuating said pressure cylinder and piston, said base frame including two spaced longitudinally extending members, said linkage means including a central support member and side stabilizing members spaced closely adjacent to said central support member, said central support member being pivotally connected between said longitudinally extending members of said base frame and said side stabilizing members being pivotally connected to the outer sides of said longitudinally extending members of said base frame, the pivotal connections of said central support member and said side stabilizing members with said longitudinally extending members being spaced from each other along said longitudinally extending members in a substantially horizontal plane, and the opposite ends of said central support member and said side stabilizing members being pivotally connected to said upper frame in a similar spaced relationship in a second horizontal plane, and said piston being pivotally connected to the end of said central support member which is pivotally connected to said longitudinally extending members of said base frame.

2. A portable adjustable animal hospital table according to claim 1 wherein said rolling means are lockable casters.

3. A portable adjustable animal hospital table according to claim 1 wherein said plastic bed surface is formed of a thermoplastic polymer.

4. A portable adjustable animal hospital table according to claim 3 wherein said thermoplastic polymer is a polyalkylene, polyamide, polyester or polyacrylic polymer.

5. A portable adjustable animal hospital table according to claim 1 wherein said plastic bed surface includes drain means.

6. A portable adjustable animal hospital table according to claim 1 wherein said upper frame includes tie-down means and an intravenous feeder hanger.

7. A portable adjustable animal hospital table according to claim 1 wherein said cylinder and piston actuating means includes a pump.

8. A portable adjustable animal hospital table according to claim 1 wherein said radiation shielding layer is a lead sheet.

9. A portable adjustable animal hospital table according to claim 2 wherein said plastic bed surface is formed of a thermoplastic polymer, said radiation shielding layer is a lead sheet, said upper frame includes slidable wing bolt tie-down means and an intravenous feeder hanger, and said cylinder and piston actuating means includes a foot-operated pump.

* * * * *